US006390971B1

(12) United States Patent
Adams et al.

(10) Patent No.: US 6,390,971 B1
(45) Date of Patent: May 21, 2002

(54) METHOD AND APPARATUS FOR A PROGRAMMABLE IMPLANTABLE HEARING AID

(75) Inventors: Theodore P. Adams, Edina; Bruce A. Brillhart, Minneapolis; Scott C. Meyerson, Moundsview, all of MN (US)

(73) Assignee: St. Croix Medical, Inc., Minneapolis, MN (US)

( * ) Notice: Subject to any disclaimer, the term of this patent is extended or adjusted under 35 U.S.C. 154(b) by 0 days.

(21) Appl. No.: 09/498,154

(22) Filed: Feb. 4, 2000

Related U.S. Application Data

(60) Provisional application No. 60/118,857, filed on Feb. 5, 1999.

(51) Int. Cl.[7] .......................... H04R 25/00; A61N 1/10

(52) U.S. Cl. .......................................... 600/25; 607/55

(58) Field of Search ............................ 600/25; 607/56, 607/57, 55, 45, 4; 381/328; 623/10

(56) References Cited

U.S. PATENT DOCUMENTS

| | | | | |
|---|---|---|---|---|
| 4,850,962 A | * | 7/1989 | Schaefer | 600/25 |
| 5,531,774 A | * | 7/1996 | Schulman et al. | 607/56 |
| 5,569,307 A | | 10/1996 | Schulman et al. | |
| 5,584,869 A | * | 12/1996 | Heck et al. | 607/57 |
| 5,721,783 A | * | 2/1998 | Anderson | 381/68.6 |
| 5,824,022 A | * | 10/1998 | Ziberman et al. | 607/57 |
| 5,993,376 A | * | 11/1999 | Kennedy | 600/25 |

FOREIGN PATENT DOCUMENTS

| | | |
|---|---|---|
| DE | 195 41 648 A | 5/1997 |
| EP | 0 340 594 A | 4/1989 |
| WO | WO 98/06237 | 2/1998 |

* cited by examiner

*Primary Examiner*—Eric F. Winakur
*Assistant Examiner*—Nikita R Veniaminov
(74) *Attorney, Agent, or Firm*—Fredrikson & Byron, P.A.

(57) ABSTRACT

The invention discloses a programmable implantable hearing aid including built-in electronics being in wireless communications with a hand-held programmer. The programmer transmits digital code signals of the type including RF, infrared and ultrasonic, based on selected parameter settings. A receiver accepts the signals for transmission to an input transducer in the middle ear. The input transducer collects the middle ear's response to the signals and transmits it to a circuit in the implanted hearing aid. The circuit searches for specific programming patterns and decodes the signals to effectuate the desired adjustment in the hearing aid. The conditioned signals are then transferred to an output transducer to operate the device at the adjusted signal level and condition. The invention enables both a patient and doctor to make unlimited number of adjustments in the implanted hearing aid without invasive surgery.

22 Claims, 4 Drawing Sheets

METHOD AND APPARATUS FOR A PROGRAMMABLE IMPLANTABLE HEARING AID

This application claims benefit of U.S. Provisional Application Ser. No. 60/118,857.

BACKGROUND OF THE INVENTION

1. Field of the Invention

The present invention relates generally to implantable hearing aid technology. Specifically, the invention pertains to a programmable hearing aid in which several parameters are adjustable by a patient and a physician after the hearing aid has been permanently implanted in the patient.

2. Description of Related Art

Several types of partially implantable hearing aids have been in use for sometime now. Although there are significant variations between these devices, the basic structural organization remains the same. Currently, very little adjustments could be made to these devices after implant. Generally, in hearing aids where the entire device is implanted there is only a one-time adjustment which is done during the time of installation. Subsequent adjustments would therefore require an invasive surgical procedure thus making continued fine tuning and real time adjustment very expensive and time consuming.

The imperatives for continued adjustment of hearing aids may primarily be driven by morphological changes in the auditory elements of the patient's ears. This may result in the hearing aid being occasionally out of tune thus needing adjustments to rectify the problem. Further, to be effective, a hearing aid must preferably be implemented to match a patient's specific needs. These needs may change over time and, as well, depend on the type of eminent auditory stimulus to which the patient is subjected. For example, a patient may at the very least be able to adjust the volume of an auditory stimulus. Moreover, the patient may elect to turn the device off, for example, and attempt to block out unwanted noise. Furthermore, the patient may elect to test the performance of the hearing aid and conduct a self-directed preliminary evaluation.

As indicated hereinabove, with the exception of invasive surgery, there are no systems known to the inventors which enable real time and non-invasive adjustments of hearing aids after implant. Accordingly, there is a need for a method and device to enable patients and physicians to adjust hearing aids, after implant, on an as needed basis.

SUMMARY OF THE INVENTION

It is one of the primary objectives of this invention to provide built-in adjustment tools and telemetry for hearing aids after permanent implant without any subsequent invasive surgery.

It is another object of this invention to provide a locally and remotely adjustable inner ear hearing aid to enable a high level of reliability and maintainability. In this regard, it is a further object of the invention to provide patient-adjustable features likely to reduce non-critical visits to the doctor while promoting patient freedom to travel and live in rural areas where a clinic or a hospital may not be readily available.

It is yet another object of the present invention to provide an external device configured to select parameters and settings, electronics for encoding the settings into, preferably, a digital pulse code modulated format, electronics for generating RF carrier for transmitting the encoded signals, and an antenna to receive the signals. The external device interfaces with an implanted hearing aid to thereby influence the functional parameters of the implanted hearing aid as needed.

It is yet another object of the invention to provide an infrared carrier to carry encoded information between the programmed and implanted hearing aid. In this configuration the transmitter/receiver (transceiver) is similar to a remote controller commonly used to program audiovisual equipment. The hearing aid is implanted subcutaneously with a window in the housing of the electronics package that is at least partially transparent to infrared signals.

Yet a further object of the present invention includes a method in which a programmer/transmitter emits ultrasonic signals which are received by ultrasonic transducer in or near the implanted electronics package. The transmitter may be touched to the skin of the patient near the receiver transducer in order to conduct the signals through the body from the transmitter to the receiver.

Yet another object of the invention includes a logic structure in which the programmer/transmitter sends encoded acoustic signals that are picked up by the ear drum and thus detected by the input transducer of the implanted hearing aid. The circuitry in the hearing aid continually checks for specific programming patterns (wake up code) in a specific frequency band of the programmer/transmitter and when detected decodes the information and makes the required changes.

Another object of the invention includes the provision of a telemetry structure including data streams. The telemetry structure uses, inter alia, pulse code telemetry and pulse interval telemetry. The data stream is formatted to instruct the receiver that data is being transmitted and that, subsequently, the data should be stored in memory upon reception.

DESCRIPTION OF THE INVENTION

Figure 1:
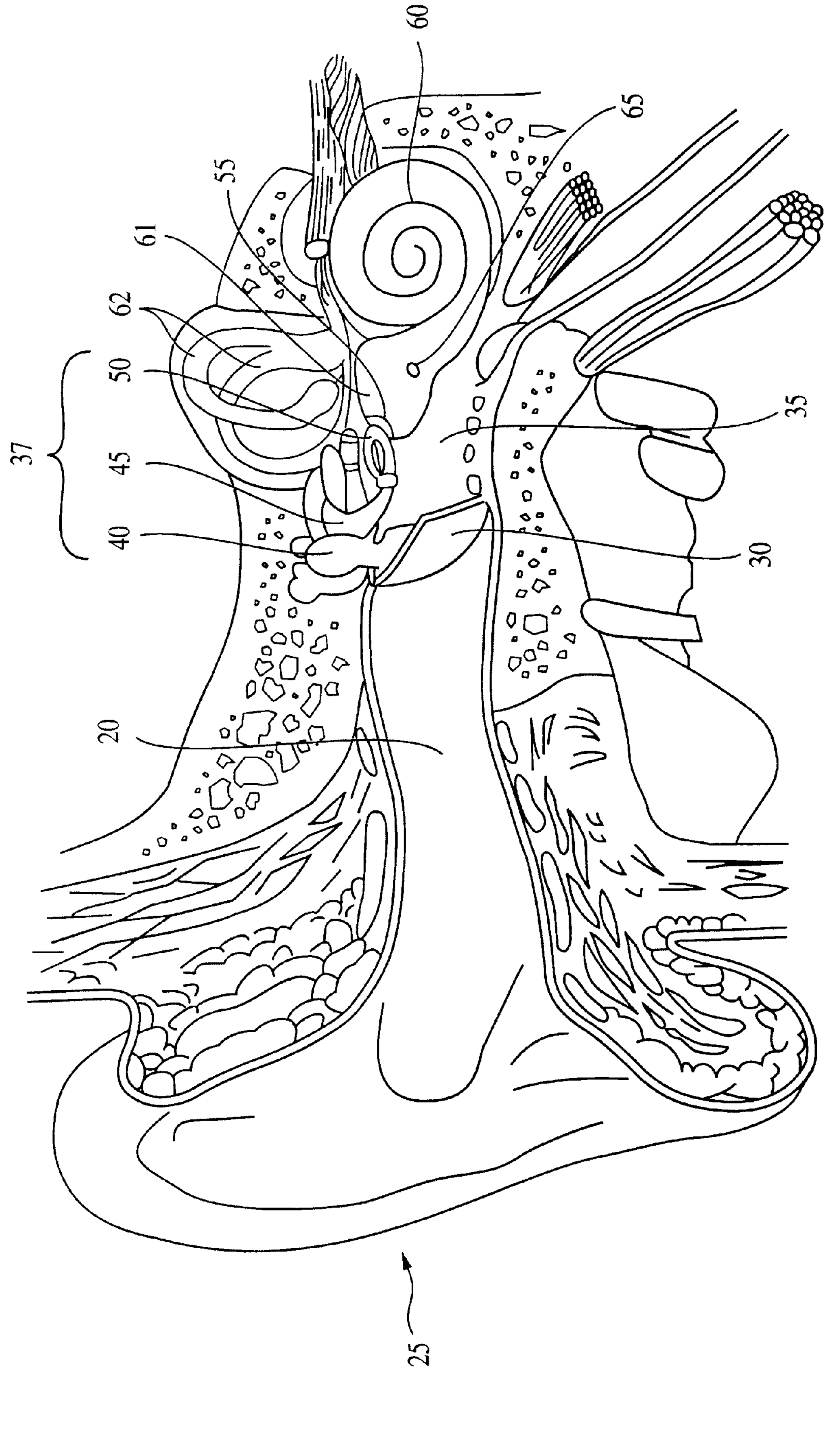
FIG. 1 illustrates a section of an anatomically normal human ear in which the present invention is implemented.

FIG. 1 illustrates, generally, the use of the invention in a human auditory system. Sound waves are directed into an external auditory canal 20 by an outer ear (pinna) 25. The frequency characteristics of the sound waves are slightly modified by the resonant characteristics of the external auditory canal 20. These sound waves impinge upon the tympanic membrane (eardrum) 30, interposed at the terminus of the external auditory canal 20, between it and the tympanic cavity (middle ear) 35. Variations in the sound waves produce tympanic vibrations. The mechanical energy of the tympanic vibrations is communicated to the inner ear, comprising cochlea 60, vestibule 61, and semicircular canals 62, by a sequence of articulating bones located in the middle ear 35. This sequence of articulating bones is referred to generally as the ossicular chain 37. Thus, the tympanic membrane 30 and ossicular chain 37 transform acoustic energy in the external auditory canal 20 to mechanical energy at the cochlea 60.

The ossicular chain 37 includes three primary components: a malleus 40, and incus 45, and a stapes 50. The malleus 40 includes manubrium and head portions. The manubrium of the malleus 40 attaches to the tympanic membrane 30. The head of the malleus 40 articulates with one end of the incus 45. The incus 45 normally couples mechanical energy from the vibrating malleus 40 to the stapes 50. The stapes 50 includes a capitulum portion, comprising a head and a neck, connected to a footplate portion by means of a support crus comprising two crura. The stapes 50 is disposed in and against a membrane-covered opening on the cochlea 60. This membrane-covered opening between the cochlea 60 and middle ear 35 is referred to as the oval window 55. Oval window 55 is considered part of cochlea 60 in this patent application. The incus 45 articulates the capitulum of the stapes 50 to complete the mechanical transmission path.

Normally, prior to implementation of the invention, tympanic vibrations are mechanically conducted through the malleus 40, incus 45, and stapes 50, to the oval window 55. Vibrations at the oval window 55 are conducted into the fluid-filled cochlea 60. These mechanical vibrations generate fluidic motion, thereby transmitting hydraulic energy within the cochlea 60. Pressures generated in the cochlea 60 by fluidic motion are accommodated by a second membrane-covered opening on the cochlea 60. This second membrane-covered opening between the cochlea 60 and middle ear 35 is referred to as the round window 65. Round window 65 is considered part of cochlea 60 in this patent application. Receptor cells in the cochlea 60 translate the fluidic motion into neural impulses which are transmitted to the brain and perceived as sound. However, various disorders of the tympanic membrane 30, ossicular chain 37, and/or cochlea 60 can disrupt or impair normal hearing.

Figure 2A:
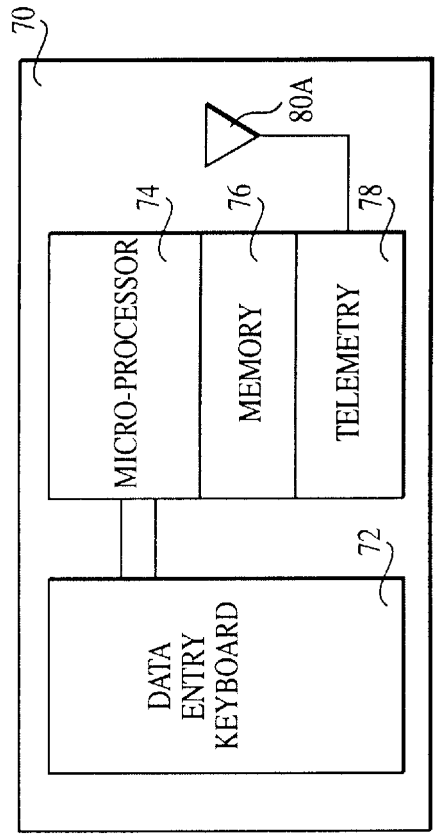
FIG. 2A is a block diagram showing the major components of a remote control programmer including an RF transmitter.
Figure 2B:
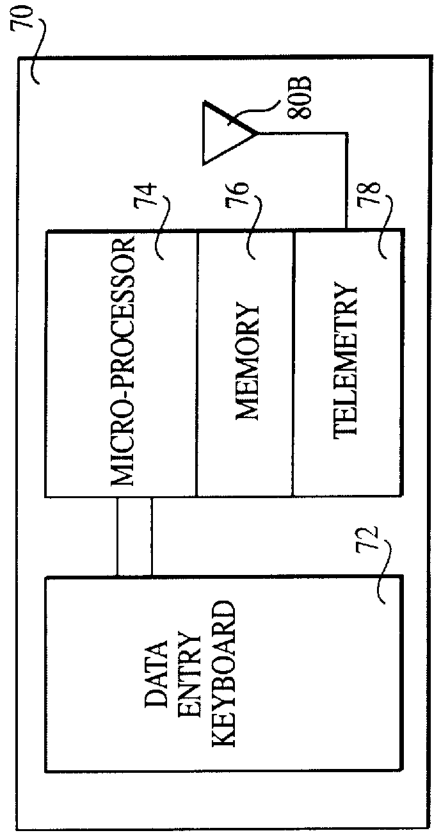
FIG. 2B is a block diagram showing the major components of a remote control programmer including an infrared transmitter.
Figure 2C:
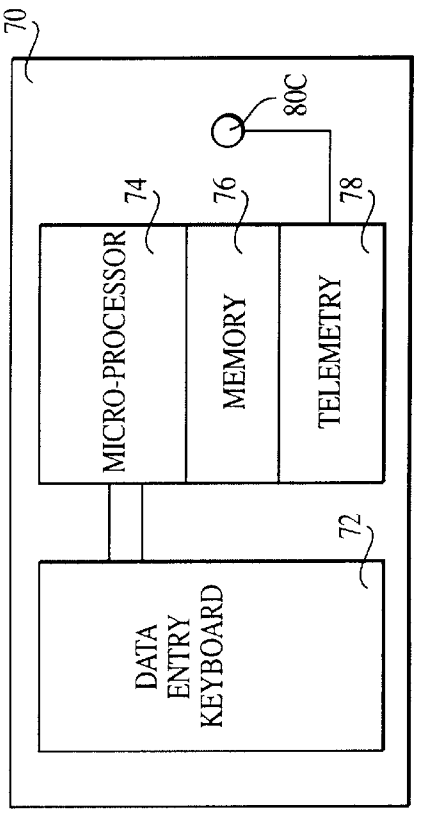
FIG. 2C is a block diagram showing the major components of a remote control programmer including an acoustic transmitter.

To provide an effective hearing aid, several parameters need to be made adjustable by the patient and the physician. At the very least the patient should be able to control volume and be able to turn the hearing aid off and on. Similarly, the physician should be able to check and or adjust gain range, filter responses, maximum power output and other parameters. FIG. 2A shows a remote controller 70 which includes data entry keyboard 72 being in data communications with microprocessor 74, memory unit 76, telemetry 78 and RF transmitter 80A. Programmer 70 is preferably adapted to be hand held. The patient or the physician can enter data/instructions at keyboard 72. Various types of signals may be used to induce a coded signal response in the hearing aid. Specifically, embodiments illustrated in FIGS. 2B and 2C use infrared and ultrasonic signals respectively. These features are provided herein as examples only and are not limiting as to the type of signals that could be used with the present invention. In FIG. 2B, infrared signal is transmitted by IR transmitter 80B. Further, in FIG. 2C, ultrasonic signal is transmitted by transmitter 80C.

Figure 3:
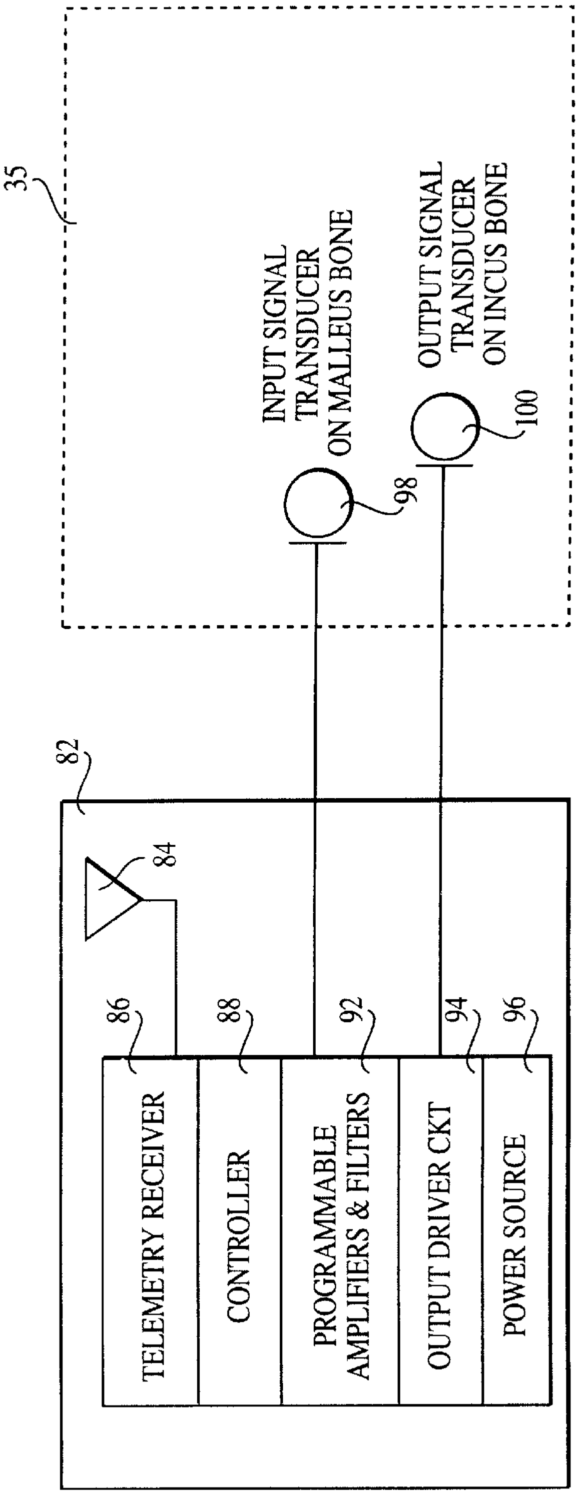
FIG. 3 is a block diagram showing the major components of the implanted hearing device.

Referring now to FIG. 3, implanted hearing aid 82 includes receiver 84, telemetry 86, controller 88, programmable amplifiers and filters 92, output driver circuit 94 and power source 96. In this embodiment, hearing aid 82 is implanted subcutaneously at about the mastoid (not shown). Generally, a subcutaneous implant, as that is used in this embodiment, involves slight anterior pulling of outer ear 25, to expose a region of the temporal bone (the mastoid). An incision is made in the skin covering the mastoid and an underlying access hole 85 is created through the mastoid allowing external access to the middle ear 35. The access hole is located approximately posterior and superior to the external auditory canal 20. By placing the access hole in this region, a transducer is disposed within the middle ear 35 cavity.

Still referring to FIG. 3, programmable amplifiers and filters 92 are connected to input signal transducer 98 which is, for example, attached to malleus 40. Further, output driver circuit 94 is connected to output signal transducer 100, attached at incus 45. Thus, when a signal is received at receiver 84, it is directed to telemetry receiver 86 and subsequently relayed to programmable amplifiers and filters 92 where the signal is filtered and adequately amplified and transmitted to input signal transducer 98 at, for example, malleus bone 140. Transducer 98 converts the signal to a vibration for perception as audible sound in the ear. An alternate output signal transducer 100 at incus bone 145 transduces the vibratory signal as feedback into output driver circuit 94. An alternate embodiment, which may be preferred according to patient need, includes an implant in the cochlear region of the patient. In such an embodiment, the functional aspects of the invention are essentially as described for the middle ear type of application also described and also claimed herein.

Referring now to FIG. 2A in more detail, RF transmitter 80A is used to send signals to hearing aid 82. The signals are representative of desired settings at which hearing aid 82 needs to be set. Receiver 84 in hearing aid 82 responsively directs the signal to programmable amplifiers and filters 92. Subsequently, the signal is directed to input signal transducer 98 attached to, for example, malleus 40 in middle ear cavity 35. Microprocessor 74, memory 76 and telemetry 78 co-operate to enable the setting, selection and encoding of the signals to transmit to hearing aid 82. The encoded signal is received at receiver 84, decoded in telemetry receiver 86 and directed to programmable amplifiers and filters 92 from where it is directed to the middle ear 35. Input transducer 98 collects the middle ear's response to the signals and provides the information to programmable amplifiers and filters 92. Thereafter, the signal is conditioned to effectuate the desired adjustment in hearing aid 82. The conditioned signal is directed to output driver circuit 94 for transfer to output transducer 100. Specifically, output driver circuit 94 searches for specific programming patterns in the signals and decodes the signals for transmission to output transducer 100 to thereby implement the desired adjustment.

Sound loudness generally depends on the intensity and frequency of the sensitivity of the patient's ear. Thus the selected parameters and settings include frequency adjustments suited to the patient's needs. The present invention provides RF, infrared, ultrasonic and equivalent encoded signals to induce a response in middle ear 35 of the patient. In the alternate embodiment shown in FIG. 2B, an infrared carrier is used to carry encoded information between programmer 70 and implanted device 82. In this embodiment, transceiver 80B is equivalent to a remote controller/programmer used in audio visual equipment. Implanted device 82 is subcutaneously implanted with a window in the housing of the electronics package. The window is at least partially transparent to infrared signals.

Another embodiment includes a structure in which programmer 70 transmits ultrasonic signals at transmitter 80C. The ultrasonic transmission is preferably received by telemetry receiver 86. Receiver 86 is adapted to receive ultrasonic signals. Subsequently, the signal is received by transducer 98 which is preferably piezoelectric. The ultrasonic signal may be transmitted at a distance. In the alternate, the patient or doctor may bring the programmer close to the skin of the patient in order to conduct the signals through the body from transmitter 80C to receiver 84.

Figure 4A:
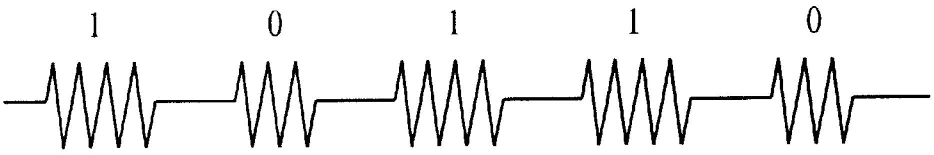
FIG. 4A illustrates pulse code telemetry.
Figure 4B:
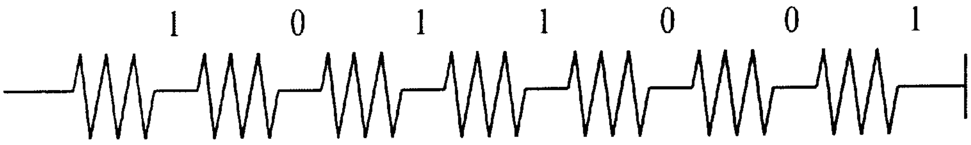
FIG. 4B illustrates pulse interval telemetry.
Figure 4C:
FIG. 4C illustrates a typical data stream.

FIGS. 4A and 4B represent encoded signals which, in the alternate embodiment, are transmitted by programmer 70. Specifically, telemetry 78 is designed to include digital data streams structured in at least one of the manners of pulse code telemetry of FIG. 4A and pulse interval telemetry of FIG. 4B. The transmitted data stream may include short bursts of carrier at fixed intervals where the width of the burst indicates the presence of a "one" or "zero". Pulse code modulation (PCM) is implemented to divide the peak-to-peak amplitude range of the signal to be transmitted. Further, the transmitted data stream may include pulse interval telemetry which includes short bursts of carrier of equal length whose interval indicates a "one" or a "zero". FIG. 4C illustrates an exemplary embodiment wherein identification (or wake up) and address components of a signal precede a data component.

Accordingly, the present invention enables adjustment of critical operational parameters after implant. In the preferred embodiment, RF receiver 84 is installed as part of the implanted hearing aid electronics. Programmer 70 sends RF signals representative of desired settings in implanted RF receiver 84. Programmer 70 includes means for selecting parameters and settings, electronics for encoding the settings into a preferably encoded digital pulse code modulated format or equivalent format such as FM, electronics for generating the encoded signals and an antenna. The system further comprises the implanted electronics which, inter alia, includes means for receiving the encoded programming signals, decoding the signals and making changes, as desired, in the functional parameters of the implanted hearing aid.

In an alternate embodiment, an infrared carrier is used to carry the encoded information between the programmer and implanted device. As discussed hereinabove, another alternate embodiment includes an infrared carrier used to carry encoded information between the programmer and implanted device. In yet another embodiment the programmer unit emits ultrasonic signals for reception by a transducer near the implanted electronics package.

Although the description of the preferred embodiment has been presented, it is contemplated that various changes could be made without deviating from the spirit of the present invention. Accordingly, it is intended that the scope of the present invention be dictated by the appended claims, rather than by the description of the preferred embodiment.

What is claimed is:

1. A hearing aid including a built-in electronics being in wireless and data communications with a programmer, the hearing aid and the programmer forming a system comprising:

an implanted electronics system;

an input and an output transducer in electrical communication with the electronics system; and the programmer including a transceiver means and telemetry means being in communications with the electronics system, the programmer including electronics for encoding settings provided thereto into a one of digital pulse code modulated format or digital pulse interval format;

wherein said implanted electronics system is adapted to be installed at least subcutaneously and said input and output transducers are adapted to be installed in an ear region of the patient wherein the programmer wirelessly communicates with the electronics system to influence operational parameters of the hearing aid.

2. The system of claim 1 wherein said programmer includes an RF signal transmitter.

3. The system of claim 2 wherein the electronics system includes a receiver for said RF signal.

4. The system of claim 1 wherein said input transducer is in electrical communication with a programmable amplifiers and filters component of said implanted electronic system.

5. The system of claim 1 wherein said output transducer is in electrical communication with an output driver circuit component of said implanted electronic system.

6. The system of claim 1 wherein the programmer includes a data entry means, a microprocessor and memory incorporated with a transceiver and a telemetry component.

7. The system of claim 6 wherein said data entry means includes means for selecting parameters and settings.

8. The system of claim 1 wherein a digital data stream is used within said telemetry means.

9. The system of claim 1 wherein the programmer includes a signal transmission means for transmitting one of ultrasonic and infrared signals.

10. In an implanted hearing aid wherein a telemetry system comprising digital data streams is implemented to send and receive signals between a circuit in the implanted hearing aid and an external programmer, the telemetry system comprising:

means for transmitting programmed signals from the programmer;

means for receiving said programmed signals in the circuit; and means for identifying and decoding specific patterns in said programmed signals, said means for transmitting and said means for receiving being in wireless communication to enable remote adjustment of the implanted hearing aid based on said specific patterns of programmed signals.

11. The system of claim 10 wherein said specific pattern includes one of pulse code telemetry and pulse interval telemetry.

12. The system of claim 10 wherein said programmed signals include at least one of RF, infrared and ultrasonic signals.

13. A method of adjusting an implanted hearing aid using a programmer being in wireless communication with the hearing aid, the method comprising the device implemented steps of:

transmitting signals having specific patterns from the programmer;

receiving the signals via a circuit in the hearing aid;

recording response signals within the middle ear via an output transducer;

analyzing the response signals from the transducer;

conditioning the response signals; and transferring to an output transducer a conditioned set of response signals to make adjustments in the hearing aid.

14. The method according to claim 13 wherein said step of transmitting signals includes a step of transmitting of one of RF, infrared and ultrasonic signals.

15. The method according to claim 13 wherein said step of receiving the signals includes a step of wireless telemetry reception.

16. The method according to claim 13 wherein said step of analyzing includes the step of decoding the response signals.

17. The method according to claim 16 wherein said step of decoding includes the steps of looking for specific programming patterns in a specific frequency band.

18. The method according to claim 17 wherein said programming pattern is implemented as a wake up code.

19. The method according to claim 17 wherein said frequency band is based on the transmission from the programmer.

20. The method according to claim 13 wherein said step of transmitting signals includes transmitting digital data streams comprising pulse code and pulse interval telemetry and further includes the step of formatting the data stream to instruct a receiver about transmission status and location of storage for the data stream.

21. A hearing aid including a built-in electronics being in wireless and data communications with a programmer, the hearing aid and the programmer forming a system comprising:

an implanted electronics system;

an input and an output transducer in electrical communication with the electronics system; and the programmer including a transceiver and telemetry components being in communications with the electronics system, wherein a digital data stream is used within said telemetry means;

wherein said implanted electronics system is adapted to be installed at least subcutaneously and said input and output transducers are adapted to be installed in an ear region of the patient wherein the programmer wirelessly communicates with the electronics system to influence operational parameters of the hearing aid.

22. A hearing aid including a built-in electronics being in wireless and data communications with a programmer, the hearing aid and the programmer forming a system comprising:

an implanted electronics system;

an input and an output transducer in electrical communication with the electronics system; and the programmer including a transceiver and telemetry components being in communications with the electronics system, wherein the programmer is adapted to send encoded acoustic signals;

wherein said implanted electronics system is adapted to be installed at least subcutaneously and said input and output transducers are adapted to be installed in an ear region of the patient wherein the programmer wirelessly communicates with the electronics system to influence operational parameters of the hearing aid.

* * * * *